United States Patent [19]

Williams et al.

[11] Patent Number: 5,625,030

[45] Date of Patent: Apr. 29, 1997

[54] METHODS FOR SYNTHESIZING OLIGOMERS CONTAINING HYDROXY ACID UNITS

[75] Inventors: Simon F. Williams, Sherborn; Oliver P. Peoples, Arlington, both of Mass.

[73] Assignee: Metabolix, Inc., Cambridge, Mass.

[21] Appl. No.: 561,139

[22] Filed: Nov. 20, 1995

Related U.S. Application Data

[63] Continuation of Ser. No. 178,141, Jan. 6, 1994, abandoned.

[51] Int. Cl.$^6$ .................... C08G 63/06; C08G 63/685; C08G 63/91; C08L 77/00
[52] U.S. Cl. ................... 528/361; 525/450; 525/419
[58] Field of Search ............... 528/361; 525/419, 525/450

[56] References Cited

U.S. PATENT DOCUMENTS

| | | | |
|---|---|---|---|
| 5,100,778 | 3/1992 | Rademacher et al. | 435/18 |
| 5,256,762 | 10/1993 | Hermes et al. | 528/361 |

FOREIGN PATENT DOCUMENTS

WO89/10931  11/1989  WIPO.

OTHER PUBLICATIONS

Shchukina, L.A., et al., "Solid phase synthesis of a tetradepsipeptide containing three hydroxy acids," *Khim. Prir. Soedin.* 3(5):358 (1967) (Abstract).

Hirama, M., et al., "Enantiospecific Syntheses of Trifunctional (R)-3-Hydroxy Esters by Baker's Yeast Reduction", *J. Chem. Soc., Chem. Commun.,* 599–600 (1983).

Houghten, R.A., et al., "Generation and use of synthetic peptide combinatonial libraries for basic research and drug discovery," *Nature,* 354:84–86 (1991).

Houghten, et al., "The Use of Synthetic Peptide Combinatoral Libraries for the Identification of Bioactive Peptides," *BioTechniques,* 13(3):412–421 (1992).

Jones, J.B., "Enzymes in organic synthesis," *Tetrahedron,* 42(13):3351–3403 (1986).

Kawaguchi, A., et al., "A New Method for the Preparation of Acvl–CoA Thioesters," *J. Biochem.,* 89.337–339 (1981).

Kerr, J.M., et al., "Encoded Combinatorial Peptide Libraries Containing Non–Natural Amino Acids," *J. Am. Chem. Soc.,* 115:2529–2531 (1993).

Knorr, R., et al., "New Coupling Reagents in Peptide Chemistry," *Tetrahedron Lett.,* 30(15):1927–1930 (1989).

Larock, R.C., "Comprehensive Organic Transformations, A Guide to Functional Group Preparations, 3, Carboxylic Acids to Esters," VCH, New York, 966–972 (1989).

March, J., Advanced Organic Chemistry, John Wiley & Sons, (1992).

Masamune, S., et al., "A General, Selective Synthesis of Thiol Esters," *Can. J. Chem.,* 53, 3693–3695 (1975).

Mergler, et al., "Peptide Synthesis by a Combination of Solid–Phase and Solution Methods I: A New Very Acid–Labile Anchor Group for the Solid Phase Synthesis of Fully Protected Fragments," *Tetrahedron Lett.,* 29(32):4005–4008 (1988).

(List continued on next page.)

*Primary Examiner*—Joseph L. Schofer
*Assistant Examiner*—Wu C. Cheng
*Attorney, Agent, or Firm*—Arnall Golden & Gregory

[57] ABSTRACT

Methods for synthesizing oligomers containing hydroxy acids, and optionally containing other types of monomers or oligomers such as amino acids, carbohydrates, nucleotides and peptides, are provided which are rapid, simple, and readily automated. The oligomers have a C-terminal and an O, S or N-terminal end. The starting hydroxy acid can be covalently bound at either the C-terminal or O, S or N-terminal end to a solid support. The bond to the solid support can be an amide, thioester, ester, phosphate, silyl ether, carbamate, benzyl ether, or other linkage that can be cleaved either chemically or enzymatically.

20 Claims, 5 Drawing Sheets

OTHER PUBLICATIONS

Midland, M.M. and Lee, P.E., "Communications," *J. Org. Chem.*, 46:3933–3934 (1981).

Mitchell, A.R., et al., "A New Synthetic Route to tert–Butyloxycarbonylaminoacyl–4–(oxymethyl)phenyl-acetamidomethyl–resin, an Improved Support for Solid––Phase Peptide Synthesis," *J. Org. Chem.*, 43:2845–2852 (1978).

Müller, H.–M. and Seebach, D., "Poly(hydroxyalkanoates): A Fifth Class of Physiologically Important Organic Biopolymers?", *Ang. Chem. Int. Ed. Engl.*, 32:477–502 (1993).

Noyori, R., "Asymmetric catalysis by chiral metal complexes," *Chemtech*, 22:360–367 (1992).

Andrus, A., et al., "Large Scale Automated Synthesis of Oligonucleotides," *Nuc. Acids Res.*, 24:41–42 (1991).

Atherton, E., et al., "Peptide Synthesis, Part 12, 3,4–Dihydro–4–oxo–1,2,3–benzotriazin–3–yl Esters of Fluorenylmethoxycarbonyl Amino Acids as Self–indicating Reagents for Solid Phase Peptide Synthesis," *J. Chem. Soc., Perkin Trans.* I, 2887–2894 (1988).

Barany, G. and Albericio, F., "A Three–Dimensional Orthogonal Protection Scheme for Solid–Phase Peptide Synthesis under Mild Conditions", *J. Am. Chem. Soc.*, 107:4936–4942 (1985).

Bayer, E., "Towards the Chemical Synthesis of Proteins," *Angew. Chem. Int. Ed. Engl.*, 30:113–129 (1991).

Boden, E.P. and Keck, G.E., "Proton–Transfer Steps in Steglich Esterification: A Very Practical New Method for Macrolactonization," *J. Org. Chem.*, 50, 2394–2395 (1985).

Chan, T.–H. and Huang, W.–Q., "Polymer–anchored Organosilyl Protecting Group in Organic Synthesis,"*J. Chem. Soc. Chem. Commun.*, 909–911 (1985).

Chen, C.–S., et al., "Quantitative Analyses of Biochemical Kinetic Resolution of Enantiomers, 2. Enxyme–Catalyzed Esterifications in Water–Organic Solvent Biphasic Systems," *J. Am. Chem. Soc.*, 109:2812–2817 (1987).

Cho, C.Y., et al., "An Unnatural Biopolymer," *Science*, 261:1303–1305 (1993).

Danishefsky, S.J., et al., "A Strategy for the Solid–Phase Synthesis of Oligosaccharides," *Science*, 260:1307–1309 (1993).

Drüfhout, J.W., et al., "Solid–Phase Synthesis and Applications of N–(S–Acetylmercaptoacetyl)Peptides," *Analytical Biochem.*, 187:349–354 (1990).

Ecker, D.J., et al.,"Rational screening of oligonucleotide combinatorial libraries for drug discovery," *Nucleic Acids Res.*, 21(8):1853–1856 (1993).

Ellington, A.D. and Szostak, J.W., "In vitro selection of RNA molecules that bind specific ligands," *Nature*, 346:818–822 (1990).

Fields, G.B. and Noble, R.L., "Solid phase peptide synthesis utilizing 9–Fluorenylmethoxycarbonylamino acids," *Int. J. Peptide Protein Res.*, 35, 161–214 (1990).

Fox, J.E., "Automated Multiple Peptide Synthesis," *London: The Biochemical Society*, 20(4):851–853 (1992).

Fyles, T.M. and Leznoff, C.C., "The use of polymer supports in organic synthesis, V. The preparation of monoacetates of symmetrical diols," *Can. J. Chem.*, 54:935–942 (1976).

Fyles, T.M., et al., "The use of polymer supports in organic synthesis, XII, The total stereoselective synthesis of cis insect sex attractants on solid phases," *Can. J. Chem.*, 55:4135–4143 (1977).

Gioeli, C. and Chattopadhyaya, J.B., "The Fluoren–9–ylmethoxycarbonyl Group for the Protection of Hydroxy–groups; Its Application in the Synthesis of an Octathymidylic Acid Fragment," *J. Chem. Soc., Chem. Commun.*, 672–674 (1982).

Rathke, M.W., "The Reparation of Lithio Ethyl Acetate, A Simple Procedure for the Conversion of Aldehydes and Ketones to β–Hydroxy Esters," *J. Am. Chem. Soc.*, 92(10):3222–3223 (1970).

Reid, G.E. and Simpson R.J., "Automated Solid–Phase Peptides Synthesis: Use of 2–(1H–Benzotriazol–1–yl)–1,1, 3,3–tetramethyluronium Tetrafluoroborate for Coupling of tert–Butyloxycarbonyl Amino Acids," *Analytical Biochem.*, 200, 301–309 (1992).

Reusch, R.N. and Sadoff, H.L., "D–( )–Poly–β–Hydroxybutyrate in Membranes of Genetcally Competent Bacteria," *J. Bacteriol.*, 156(2):778–788 (1983).

Reusch, R.N. and Sadoff, H.L., "Putative structure and functions of a poly–β–hydroxybutyrate/calcium polyphosphate channel in bacterial plasma membranes," *Proc. Natl. Acad. Sci. USA*, 85:4176–4180 (1988).

Rink, H., "Solid phase synthesis of protected peptide fragments using a trialkoxy–diphenylmethylester resin," *Tetrahedron Lett.*, 28(33):3787–3790 (1987).

Rivaille, P., et al., "Synthesis of LH–RH using a new phenolic polymer as solid support and BOP reagent for fragment coupling," *Tetrahedron*, 36:3413–3419 (1980).

Schön, I. and Kisfaludy, L., "9–Fluorenylmethyl Pentafluorophenyl Carbonate as a Useful Reagent for the Prepoaration of N–9–Fluorenylmethyloxycarbnylamino Acids and their Pentafluorophenyl Esters," *Synthesis*, 303–305 (1986).

Schultz, S. and Toft, S., "Identifaction of a Sex Pheromone from a Spider," *Science*, 260, 1635–1637 (1993).

Seebach, D., et al., "18, High–Yield Synthesis of 20–.24–, and 28–Membered Macropentolide, –hexolide, and –heptolide, Respectively, from (R)–or S)–3–Hydroxybutanoic Acid under Y " *Helv. Chim. Acta*, 71, 155–167(1988).

Seebach, D., et al., "Biological–Chemical Preparation of 3–Hydroxycarboxylic Acids and Their Use in EPC–Syntheses," *Stereochemistry of Organic and Boorganic Transformation Workshop Conferences*, Hoechst, W. Bartmann and K.B. Sharpless (eds.), VCH Verlags–gesellschaft Weinheim, 17, S.85–126 (1987).

Shimizu, M., "Pantothenic acid and coenzyme A: Preparation of CoA analogs," *Methods in Enzymology*, 18;322–338 (1970).

Shirakura, Y., et al., Biochem. Biophys. Acta, 880, 46–53 (1986).

Simon, R.J., et al., Proc. Natl. Acad. Sci. USA, 89, 9367–9371 (1992).

Tam, J.P., et al., "$S_N2$ Deprotection of Synthetic Peptides with a Low Concentration of HF in Dimethyl Sulfide: Evidence and Application in Peptide Synthesis," *J. Am. Chem. Soc.*, 105(21):6442–6455 (1983).

Vu, H., et al., "New Reagents and Solid Support for Automated Oligonucleotide Synthesis," *Nuc. Acids Res.*, 22:63–64 (1990).

Wang, S.–S., "p–Alkoxybenzyl Alcohl Resin and p–Alkoxybenzyloxycarbonylhydrazide Resin for Solid Phase Synthesis of Protected Peptide Fragments," *J. A. Chem. Soc.*, 95(4):1328–1333 (1973).

Wieland, T. and Rueff, L., "Synthese von S–β–Oxybutyryl und S–Acetacetyl–Coenzym A." *Angew. Chem.*, 65(7):186–187 (1953).

Whitesides, G.M. and Wong, C.-H., "Enzymes as Catalysts in Synthetic Organic Chemistry," *Agnew. Chem. Int. Ed.*, 24(8):617–638 (1985).

Yamada, S., et al., "A New Synthesis of Thiol Esters," *J. Org. Chem.*, 39(22):3302–3303 (1974).

Vu, H., et al., "Large scale automated synthesis of oligonucleotides," Eighteenth Symposium on Nucleic Acids Chemistry, Sendai, Japan, Oct. 29–31, 1991. *Nucleic Acids Symposium Series*, 25:169–170 (1991).

Voss, J., "Synthesis of Thioesters and Thiolactones," *Comprehensive Organic Synthesis*, Trost, B.M. (ed.), Oxford, 6:435–460 (1991).

Pr = protecting group

Pr = protecting group

METHODS FOR SYNTHESIZING OLIGOMERS CONTAINING HYDROXY ACID UNITS

This is a continuation of application Ser. No. 08/178,141 filed on Jan. 6, 1994 abandoned.

BACKGROUND OF THE INVENTION

The present invention is in the field of polymer chemistry, specifically in the area of methods for rapidly and automatically synthesizing oligomers containing hydroxyacid monomers.

A major focus of current pharmaceutical, chemical and biological research lies in the development of high throughput screening technology in which very large numbers of chemical structures are analyzed for biological activity in automated assay systems. For example, using state-of-the-art robotics, Oncogene Science, Inc. (Uniondale, N.Y.) can screen up to 125,000 compounds a year using one automated system.

The major pharmaceutical and agrochemical companies have developed libraries of millions of different compounds to feed into screening programs. However, with the new screening techniques, the rate determining step in discovering new biologically active molecules is fast becoming the supply of new chemical candidates rather than the assay limitations. For this reason, the search for alternative and improved methods to produce large numbers of compounds for screening has increased.

Natural product discovery, wherein new chemical compounds are extracted from resources such as plants, fungi and microbes is one approach to providing new biologically active molecules. A second approach, often termed "combinatorial," relies on chemical and biological techniques to produce random libraries of compounds from a defined set of building blocks. Methods have been developed which generate: peptide libraries (Houghten, R. A., et al., Nature, 354, 84–86 (1991)), including peptide libraries containing non-natural amino acids (Kerr, J. M., Banville, S. C. and Zuckermann, R. N., J. Am. Chem. Soc., 5, 2529–2531 (1993)); peptoid libraries (Simon, R. J., et al., Proc. Natl. Acad. Sci. USA, 89, 9367–9371(1992)); oligonucleotide libraries (Ecker, D. J., et al., Nucleic Acid Res., 21, 1853–1856 (1993); Ellington, A. D. and Szostak, J. W., Nature, 346, 818–822 (1990)); and oligocarbamate libraries (Cho, C. Y., et. al., Science, 261, 1303–1305 (1993)). Methods for producing oligosaccharide libraries are also being developed (Danishefsky, S. J., et al., Science, 260, 1307–1309 (1993)).

The appeal of the combinatorial approach for generating large numbers of new and varied peptides for screening is readily appreciated by calculating the number of possible combinations of the twenty natural L-amino acids for short peptides. For six-residue peptides (termed hexapeptides) there are 64 million different combinations ($20^6$), and for seven residue peptides this number increases to 1.28 billion different combinations ($20^7$). Individually synthesizing 64 million different hexapeptides is impractical. The combinatorial approach to generating new compounds, coupled to an iterative selection process, allows identification of biologically interesting oligomers from a mixture of peptides that are heterogeneous at one or more positions in the peptide. Houghten, et al., Biotechniques, 13, 412–421 (1992), recently reported an iterative selection procedure that identified an antigenic determinant of a peptide recognized by a monoclonal antibody from a library of over 52 million hexapeptides, with approximately 500 assays.

It would be advantageous to create a new class of randomized oligomers in addition to the peptide, peptoid, oligonucleotide, oligocarbamate and oligonucleotide libraries currently being developed.

Natural polymers containing hydroxy acids have been known for a long time, as recently reviewed by Müller, H. -M. and Seebach, D., Ang. Chem. Int. Ed. Engl., 32, 477–502 (1993). These poly(hydroxyacids), termed PHAs, are synthesized by microorganisms for use as storage materials, and have been identified in bacterial membranes and in the tissues of plants and animals (Reusch, R. N. and Sadoff, H. L., J. Bacteriol., 156, 778–788 (1983)). More recently, PHAs have also been detected in human blood plasma where the biopolymer is bound to low density lipoprotein and also to albumin (Reusch, R. N. and Sadoff, H. L., Proc. Natl. Acad. Sci. USA, 85, 4176–4180 (1988)). Certain hydroxyacid dimers also have biological activity. Dimers of (R, R)-hydroxybutyrate act as pheromones in certain species of spiders from the Linyphia family. Schultz, S. and Toft, S., Science, 260, 1635–1637 (1993).

Oligomers of one hydroxy acid, (R)-3-hydroxybutyric acid, have been synthesized by partially degrading/depolymerizing poly[(R)-3-hydroxybutyrate] (PHB), and by polymerizing monomeric derivatives using conventional solution-phase techniques (Seebach, D., et al., Helv. Chim. Acta, 71, 155–167 (1988); Shirakura, Y., et al., Biochim. Biophys. Acta, 880, 46–53 (1986)).

With the availability of new screening techniques, iterative selection processes, and numerous hydroxy acid starting materials, it would be beneficial to have methods for generating random oligomers containing hydroxy acid monomers for biological, chemical and pharmaceutical evaluation.

It is therefore an object of the present invention to provide methods for synthesizing oligomers containing hydroxy acid monomers which can be automated.

It is a further object of this invention to provide methods for creating oligomers containing hydroxy acid monomers which can be used in solution-phase or in solid-phase.

It is another object of the present invention to provide methods for creating oligomers containing hydroxy acid monomers which is simple, rapid, and efficient.

It is a still further object of the present invention to provide a method for synthesizing oligomers containing hydroxy acid monomers which contain biologically active units such as sugars, nucleotides, amino acids, and oliogomers thereof.

SUMMARY OF THE INVENTION

Methods for simply and rapidly synthesizing oligomers containing hydroxy acids, and optionally containing other types of molecules such as amino acids, sugars, nucleotides, and oligomers thereof are described for use with automated synthesizers. The oligomers can be synthesized by solution-phase or solid-phase synthesis methods, although are preferably synthesized on a solid-phase.

Oligomers containing only hydroxy acid units have a C-terminal and an O-terminal end. Oligomers incorporating terminal thio acids or amino acids can have an S-terminal or N-terminal end. The oligomers are prepared by protecting either the C-terminal end, and reacting the free hydroxy (or thio or amine) group with a carboxylic acid or derivative thereof on a molecule to be incorporated into the oligomer, or by protecting the hydroxy (or thio or amine) group and reacting the free carboxy group with a hydroxy (or thio or amine) group on a molecule to be incorporated into the oligomer. If the resulting oligomer is to be further elongated, the molecule to be incorporated into the oligomer must have a protected functional group, such as hydroxy, carboxy, thio, or amine, capable of reacting with another monomer, respectively, which is deprotected after the initial coupling reaction.

The method is particularly well suited for use with commercially available apparatus such as a peptide synthesizer. In a preferred embodiment, the starting monomer is coupled to a solid support which is removed by cleaving after the oligomer is synthesized. The starting hydroxy acid monomer can be covalently bound to the solid support at either the C-terminal or O, S or N-terminal end. The bond to the solid support can be an ester, amide, thioester, carbamate, phosphate, silyl ether, benzyl ether, or other linkage that can be cleaved either chemically or enzymatically.

The resulting oligomers can be screened for biological activity by techniques known to those skilled in the art.

DETAILED DESCRIPTION OF THE INVENTION

Oligomers containing hydroxy acid monomers are prepared by solution-phase or solid-phase synthesis in an easily automated process. In either solid phase or solution phase synthesis, two molecules containing both a carboxyl group and a hydroxy, thio, or amine group are covalently linked by forming an ester, thioester or amide bond. The carboxy group on one of the molecules, and the hydroxy, thio or amine group on the other molecule is protected before the reaction. Protecting these groups ensures that each molecule can only react with the other molecule. One can then selectively deprotect either the carboxyl group or the hydroxy, thio or amine group, depending on in which direction the oligomer is going to be elongated, and covalently link the molecules. Resulting oligomers can contain different hydroxy acids, can contain the same hydroxy acids (homo-oligomers), and optionally can incorporate any number of biologically active molecules.

In the solution-phase approach, both molecules are placed in solution, the coupling and deprotection steps are performed, and the process is repeated until the desired oligomer is produced. However, in order to obtain pure oligomers, several isolation steps must be used to remove excess reagents, deprotected groups and other impurities from the oligomer.

In a solid-phase approach, the starting material is covalently attached to a solid support. After the coupling and deprotecting reactions are done, excess reagents, deprotected groups and other soluble impurities are washed away from the solid support. Importantly, since there is no purification until the oligomer is removed from the solid support, complete reaction of the attached molecule must be ensured at each step. It is advantageous to use excess reagents.

Solid-phase synthesis of oligomers containing hydroxy acid monomers is preferred to solution-phase synthesis since the synthesis is simpler and faster, losses due to isolation and purification of intermediates are avoided, and high yields (typically greater than 85% for each addition involving a deprotecting and coupling step) are obtained. Increased solvation and decreased aggregation of the intermediates are also possible. Most importantly, it is readily automated.

The solid-phase synthesis of an oligomer made from hydroxy acid monomers involves the following key steps.

1. Protecting the carboxyl group at the C-terminal end of a first monomer.
2. Protecting the hydroxyl group at the O-terminal end of a second monomer, wherein the protecting group at either the C-terminal or O-terminal end is attached to a solid support.
3. Protecting any side-chain functional groups on the hydroxy acids, if necessary.
4. Using a coupling agent, or equivalent means, to form an ester bond between the unprotected ends of the hydroxy acid monomers.
5. Repeating either step 1 or 2 and steps 3 and 4 until an oligomer of the appropriate length and composition is formed.
6. Optionally incorporating other molecules into the oligomer.
7. Deprotecting the side-chain functional groups.
8. Optionally removing the oligomer from the solid support.

A. Selection of Oligomer Components.
1. Hydroxy Acid Monomers.

The oligomers described herein are prepared from monomers of the formula wherein
$R^1$ is, independently, H, straight chain or branched $C_1$–$C_{20}$ alkyl, alkenyl, alkynyl, aryl, alkaryl, aralkyl, alkyloxyalkyl, aryloxyalkyl, C(O)alkyl, C(S)alkyl, C(NR$^3$)alkyl, C(O)aryl, C(S)aryl, C(NR$^3$)aryl, C(O)alkaryl, C(S)alkaryl, C(NR$^3$)alkaryl, C(O)aralkyl, C(S)aralkyl, C(NR$^3$)aralkyl, C(O)alkyloxyalkyl, C(S) alkyloxyalkyl, C (NR$^3{}_2$)alkyloxyalkyl, C(O) acyloxyalkyl, C(S) acyloxyalkyl, C(NR$^3$)acyloxyalkyl, or P(O)$_m$(OR$^3$);

$R^2$ is —OH, $R^3$ is H, $C_1$–$C_{20}$ straight chain or branched alkyl, aryl, or substituted silyl;

m is 0, 1 or 2, n is between 0 and 25, and $R^1$ is optionally substituted with heteroatoms, amines, hydroxyl, carboxyl, sulfhydryl, sulfate, phosphonate, phosphate, or phosphinate groups.

As used herein, the term "substituted silyl" refers to trialkyl silyl such as trimethyl silyl, dialkylaryl silyl, such as phenyldimethyl silyl, diarylalkyl silyl, such as t-butyldiphenyl silyl, or triaryl silyl, such as triphenyl silyl.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

As used herein, the term "aralkyl" refers to an aromatic ring substituted with one to five $C_1$–$C_{50}$ straight chain or branched alkyl groups.

As used herein, the term "alkaryl" refers to a $C_1$–$C_{50}$ straight chain or branched alkyl group substituted with one or more aryl groups.

Hydroxy acid monomers can be isolated from nature or prepared using chemical techniques, biological techniques, or both of these techniques, as described, for example, in Seebach, D., Roggo, S. and Zimmermann, J., Workshop conferences, Hoechst, W. Bartmann and K. B. Sharpless (eds.), VCH Verlagsgesellschaft, Weinheim, Vol. 17, S.85–126 (1987); Rathke, M. W., J. Am. Chem. Soc., 92, 3222–3223 (1970); Müller, H. -M. and Seebach, D., Ang. Chem. Int. Ed. Engl., 32, 477–502 (1993); Noyori, R., Chemtech, 22, 360–367 (1992); Hirama, M., Shimizu, M. and Iwashita, M., J. Chem. Soc., Chem. Commun., 599–600 (1983); Midland, M. M. and Lee, P. E., J. Org. Chem., 46, 3933–3934 (1981); and references therein. Certain hydroxy acid monomers are commercially available. The hydroxy acid monomers can be chiral or achiral. In addition, the hydroxy acid monomers can be substituted, unsubstituted or derivatized. Oligomers of 2-, 3-, 4-, and 5-hydroxy acids are particularly preferred for biological applications.

2. Incorporation of Non-hydroxy acids into the Oligomer.

As used herein, the term "biologically active molecules" includes nucleotides, amino acids, sugars, thio acids, lipids, fatty acids, and other biologically active organic and inorganic molecules such as steroids, and oligomers thereof, which potentially have or result in the oligomer having biological activity in an assay for therapeutic activity, for example, these molecules may have activity as coenzymes, hormones, receptors, neuromodulators, chelators, biomodulators or effector molecules.

These molecules can be incorporated into the hydroxy acid oligomer, either as a single unit inserted one or more times into the oligomer, or as oligomers inserted one or more times into the hydroxy acid oligomer.

The formation of oligomers containing hydroxy acids involves formation of ester, and, optionally, thioester or amide linkages. These linkages can be formed by reacting a hydroxy, thio or amine group with a carboxylic acid or a carboxylic acid derivative of the formula:

wherein $R^4$ is O; $R^5$ is $C_1$–$C_{50}$, preferably $C_1$–$C_{12}$, straight chain or branched alkyl, aryl, aralkyl, alkyl, alkyaryl, and substituted silyl; $R^6$ is halogen, $OR^3$, $SR^3$, $NR^3_2$, o- or aryloxy. For example, for amino acids, $R^6$ is OH, and $R^5$ is $H_2N$—$CR^1$—$(CH_2)n$—; for thio acids, $R^6$ is OH and $R^5$ is HS—$CR^1$—$(CH_2)n$—.

Other carboxylic acid derivatives known to those skilled in the art can also be used.

As described in more detail below, any reactive functional group not involved in the coupling chemistry must first be protected to avoid unwanted side reactions. After the carboxylic acid or derivative reacts with a hydroxy, thio, or amine group to form an ester, thioester, or amide, any protected functional groups can be deprotected by means known to those skilled in the art.

B. Coupling of Monomers

Figure 1A:
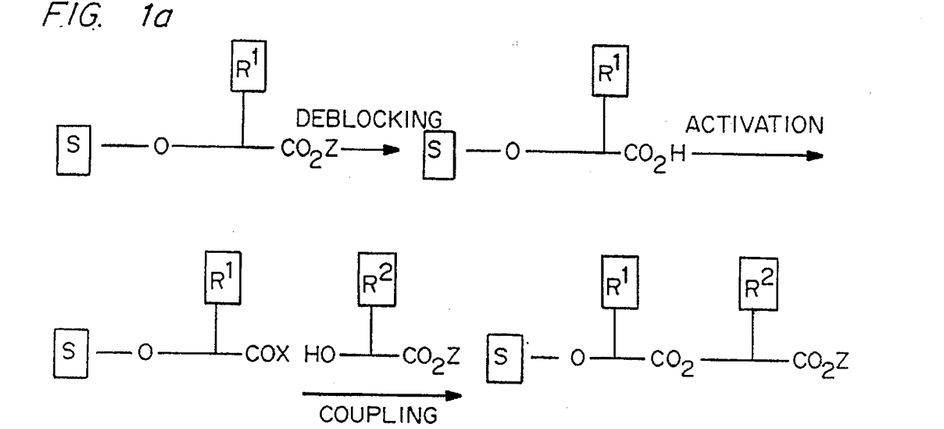
FIGS. 1a and 1b are schematic illustrations of methods of elongating either a C-terminal (FIG. 1a) or O-terminal (FIG. 1b) oligomer, using solid-phase synthesis.
Figure 1B:
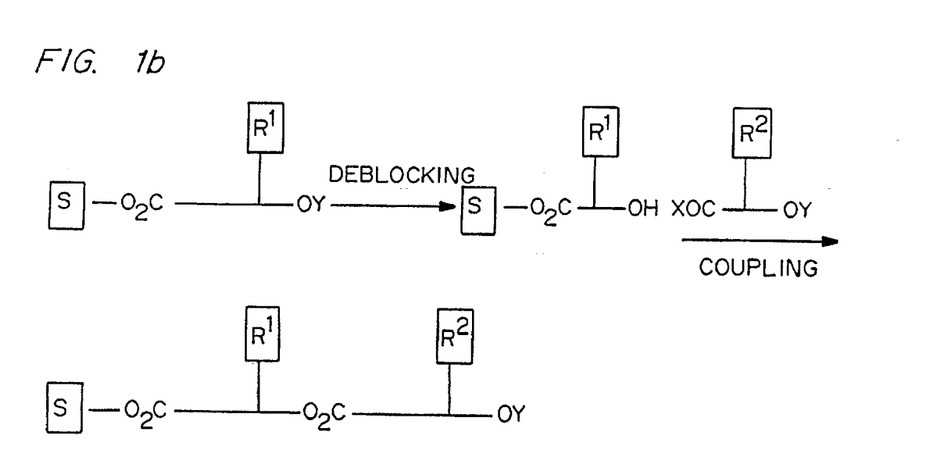
Figure 2A:
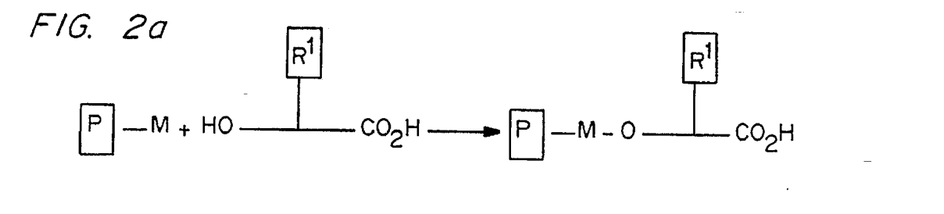
FIGS. 2a and 2b are schematic illustrations of methods of attaching the O-terminal end (FIG. 2a) or the C-terminal end (FIG. 2b) of an oligoester to a solid support.
Figure 2B:
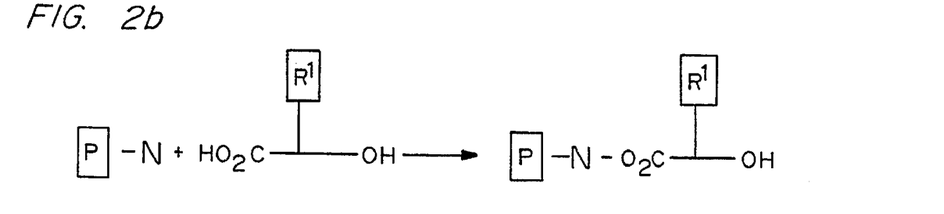

Monomers are added to form a polymer of at least two, more preferably at least three, four or five units, up to a length of about fifty to one hundred units, preferably around fifty units. Chain elongation can take place either so that hydroxy acid monomers are added to the C-terminal end or to the O-terminal end, as shown in FIGS. 1a and 1b. If C-terminal elongation is selected, as shown in FIG. 1a, then O-terminal and side-chain protecting groups must be used that are compatible with the need to remove the C-terminal protecting group for further coupling with other residues. Conversely, if O-terminal elongation is selected, as shown in FIG. 1b, then C-terminal and side-chain protecting groups must be used that are compatible with the need to remove the O-terminal protecting group for addition of further residues. Protecting groups are discussed in more detail below. In both cases, all the protecting groups must be chosen so that they can be removed at the end of the oligomer synthesis in the presence of the ester bond(s) formed during coupling. In C-terminal addition, the O-terminal end is anchored via a protecting group to a solid-phase support, whereas in O-terminal addition, the C-terminal end is anchored, as shown in FIGS. 2a and 2b, respectively. In the ideal case, the side-chain protecting groups and the O-terminal or C-terminal linkage to the solid support, respectively, should be stable to all conditions except the final deprotecting step which releases the free oligomer. For certain applications it may not be necessary to release the oligomer from the anchoring solid support.

In general, similar coupling reactions are used to link two monomers as to link a monomer to a solid support. The reagents and conditions will vary depending on the monomers to be coupled.

1. Activation of carboxyl group.

Carboxyl groups are preferably activated prior to coupling. Methods available for activating a carboxyl group for coupling to a hydroxyl, thio or amine group to form an ester, thioester or amide linkage vary from traditional methods such as intermediate acid chloride, acid anhydride, and acyl azide formation, to more sophisticated methods involving mixed anhydrides and active esters. Representative methods are listed in Larock, "Comprehensive Organic Transformation, VCH, New York, 966–972 (1989), hereby incorporated by reference. The use of intermediate acid chlorides for the solution-phase synthesis of oligomers of 3-hydroxybutyric acid is described by Seebach, D., et al., Helv. Chim. Acta, 71, 155–167 (1988). A representative method for preparing acid chlorides is to react a carboxylic acid with thionyl chloride, preferably in benzene or toluene with a catalytic amount of DMF. An exemplary method for preparing anhydrides is to react a carboxylic acid with acetic anhydride. As acetic acid is formed, it can be distilled out of the reaction vessel.

The use of N-N'-Dicyclohexylcarbodiimide (DCC) and other carbodiimides as activation reagents in peptide synthesis is well known. This reagent may also be used for activating the carboxyl group. DCC is used with a catalytic amount of 4-(N-N-dimethylamino)pyridine (DMAP) in the solution-phase synthesis of oligomers of 3-hydroxybutyric acid described by Shirakura, Y., et al., Biochim. Biophys. Acta, 880, 46–53 (1986). Other examples of dehydrating agents which can be used instead of DCC are described in March, J., Advanced Organic Chemistry, John Wiley & Sons, (1992), hereby incorporated by reference.

Other reagents used in peptide synthesis which may be used for carboxyl activation of hydroxy acid monomers, under specified conditions, include pentafluorophenyl esters (Schön, I. and Kisfaludy, L., Synthesis, 303–305 (1986)) and 1-oxodihydrobenzotriazinyl(Dhbt) esters (Atherton, E., et al., J. Chem. Soc., Perkin Trans. I, 2887–2894 (1988); Rivaille, P., Gautron, J. P., Castro, B. and Milhaud, G., Tetrahedron, 36, 3413–3419 (1980); Knorr, R., et al., Tetrahedron Lett., 30, 1927–1930 (1989)), the teachings of which are hereby incorporated by reference.

The use of benzotriazol-1-yl derivatives such as 2-(1H-Benzotriazol-1-yl)-1,1,3,3-tetramethyluronium tetrafluoroborate is preferred to DCC to minimize racemization, if chiral intermediates are used, and also to increase the reaction kinetics, as described in Reid, G. E. and Simpson, R. J., Ann. Biochem., 200, 301–309 (1992).

2. Coupling of Activated Carboxylic acid and Hydroxy Group.

The procedures used for ester bond formation between a first and a second hydroxy acid monomer are fundamentally the same regardless of whether the oligomer is extended from the carboxyl terminal or the hydroxyl terminal, as shown by FIGS. 1a and 1b. The main differences center on the choices of protecting groups.

As shown in FIG. 1a and discussed in more detail below, the carboxyl protecting group (Z) of the support-bound oligomer is selectively removed, and the resulting carboxyl component activated by a group X. The activated oligomer is then reacted with a hydroxy acid or a carboxyl-masked hydroxy acid to give the next protected oligomer. In an analogous manner, this protected oligomer can be further extended with subsequent rounds of deblocking, activation and coupling of new monomers.

As shown in FIG. 1b and discussed in more detail below, the hydroxyl protecting group (Y) of the support bound oligomer is selectively removed and the resulting hydroxyl group condensed with an activated hydroxyl-masked hydroxy acid to give the corresponding protected oligomer.

Several methods can be used to couple the activated carboxylic acid and the hydroxy group. For example, one can use the coupling reaction between a carboxylic acid and a hydroxy group described by Shirakura, et al., *Biochemica et Biophysica Acta*, Vol. 880, p. 47 (1986), in which the hydroxy group of the t-butyldimethylsilyl ether of D-(−)-3-hydroxybutyric acid was coupled with the carboxy group of a diacid in which one of the carboxy groups was protected as a benzyl ester. Approximately 1.3 equivalents of 1,3-dicyclohexylcarbodiimide (DCC) and approximately 0.1 equivalents of 4-dimethylaminopyridine (DMAP) was added to a cooled (0° C.) 2.5 M dichloromethane solution of the O-protected hydroxy acid and the diacid. The mixture was stirred at room temperature for 24 hours, ether was added, and the mixture was cooled to 0° C. for thirty minutes. The solution was filtered and the filtrate was concentrated in vacuo. Chromatography yielded 85% of the desired compound.

3. Incorporation of thio acids or amino acid monomers.

The exact method of ester, thioester or amide bond formation will depend on a number of factors, including the composition of the monomers to be incorporated into the oligomer, and monitoring requirements. Use of active esters are preferred, since they can normally be prepared in advance, stored for reasonable lengths of time without decomposition, typically six months and provide good yields of product above 80% in acceptable reaction times, for example, between two and 24 hours.

Thio acid or amino acid monomers can be incorporated into the oligomer using the coupling chemistry described above for thioester or amide coupling instead of ester coupling, whether elongating the oligomer from the C-terminal or O-terminal ends. The main differences between ester formation and thioester or amide formation include the choice of solvent and protecting group for the chemistry.

Reactions of carboxyl derivatives with hydroxy or thio groups must be carried out with aprotic solvents, to avoid reaction of the derivative with the solvent. Preferred solvents include dialkyl formamides, such as dimethylformamide, dialkyl sulfoxides, such as dimethylsulfoxide, aromatic solvents such as benzene, toluene, and xylenes, chlorinated solvents such as dichloromethane, chloroform, and trichloroethane, and ethers such as tetrahydrofuran and dibutyl ether. Use of stoichiometric amounts of trialkyl amines, pyridine, or other aprotic bases as acid scavengers is preferred.

In the case of O-terminal elongation, the thio or amine group on the molecule to be incorporated is protected, and the hydroxy group on the oligomer is reacted with the carboxy group on the thio or amino acid. After the coupling is complete, the thio or amine group is deprotected, and reacted with the carboxylic acid or derivative thereof of the next molecule to be incorporated.

In the case of C-terminal elongation, the carboxy group on the molecule to be incorporated is protected, and the thio or amine group is reacted with the carboxy group on the oligomer. After the coupling is complete, the carboxy group is deprotected, and reacted with the hydroxy, thio or amine group on the next molecule to be incorporated.

Thioester linkages can be formed by dehydrating a thiol group and a carboxylic acid using the conditions as described above for ester formation. For example, in a typical procedure for forming thioesters, triethylamine (approximately 2 equivalents) is added with stirring and cooling to a mixture of a carboxylic acid, diethyl phosphorocyanidate (DEPC) or diphenyl phosphorazidate (DPPA) (approximately 2 equivalents), and a thiol (approximately 1.2 equivalents) in dimethylformamide (DMF). A typical concentration of the acid in DMF is approximately 1 M. The reaction is typically complete within three hours at room temperature. Workup procedures typically include washing the mixture with a weak acid solution, then neutralizing the acid with carbonate or bicarbonate. Typical yields are in excess of 85%.

Amide linkages can be formed by dehydrating an amine group and a carboxylic acid using the methods described above. In a typical reaction, a solution containing a carboxylic acid (one equivalent) and an amine (slight excess) are added to a room temperature solution of DCC (slight excess) in dichloromethane (typically 0.1 M). The reaction is typically complete within an hour. Typical workup procedures include removing excess reagents with a dilute acid wash. Typical yields are greater than 75%.

It is also possible to form ester and amide bonds using enzymes such as proteases, amidases or lipases which function under specified conditions in a synthetic manner, as described by Chen, C. -S., et al., J. Am. Chem. Soc., 109, 2812–2817 (1987), hereby incorporated by reference.

4. Incorporation of nucleotides or sugar monomers.

Nucleotides and sugars can also be incorporated into the oligomer backbone, whether elongating the oligomer from the C-terminal or O-terminal ends. Nucleotides and sugars contain several hydroxy groups. Those hydroxy groups that are not involved in the desired coupling reaction must be protected to avoid interference with the oligomer synthesis, as discussed in more detail below.

Figure 3A:
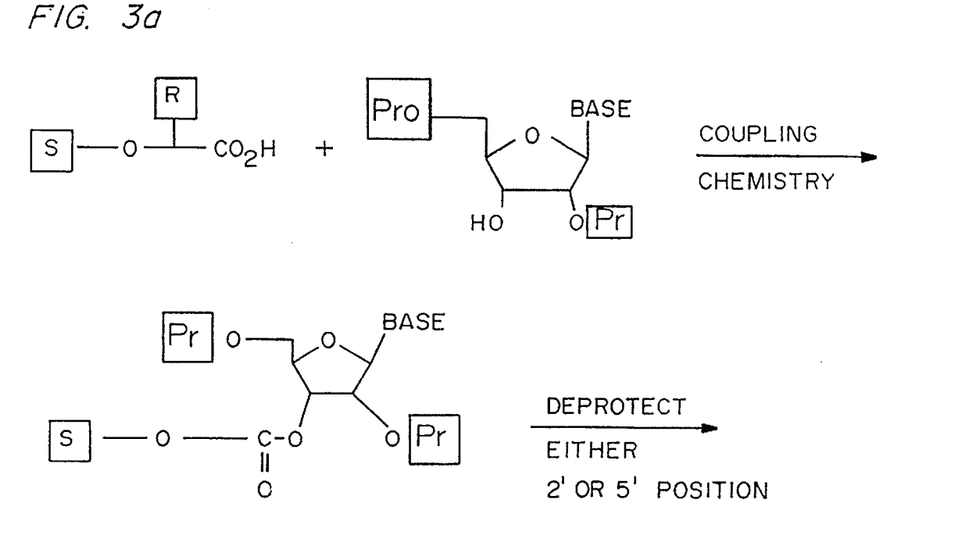
FIGS. 3a and 3b is a schematic illustration of a process for incorporating a nucleotide into an oligomer, with synthesis from either the C-terminal end (FIG. 3a) or O-terminal end (FIG. 3b).
Figure 3B:
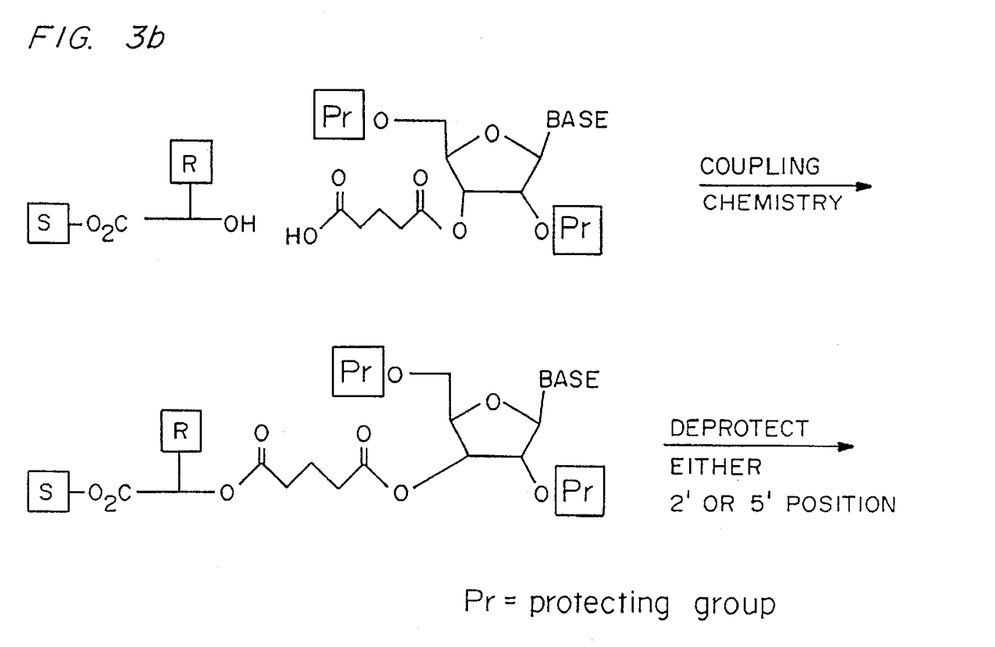
Figure 4A:
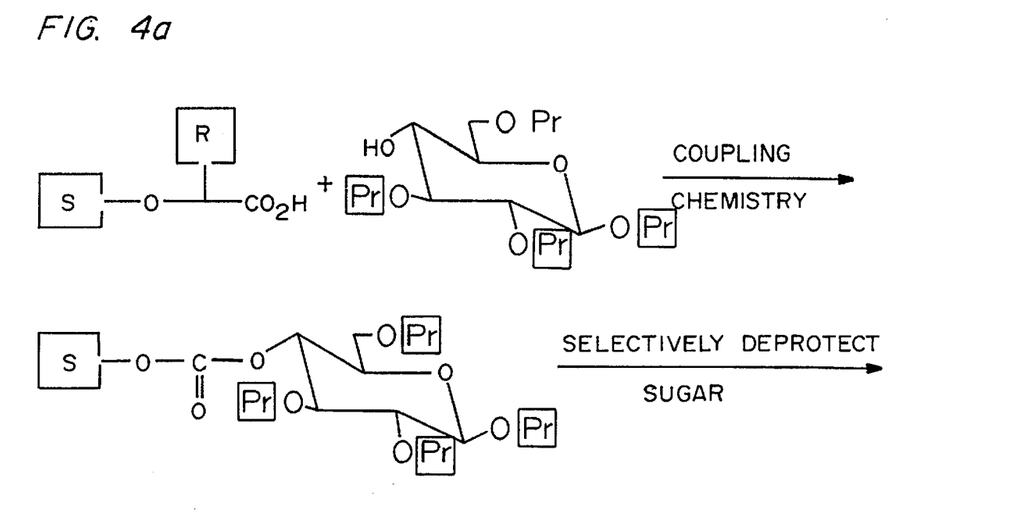
FIGS. 4a and 4b are schematic illustrations of a process for incorporating a sugar into an oligomer, with synthesis from the C-terminal end (FIG. 4a) or the O-terminal end (FIG. 4b).
Figure 4B:
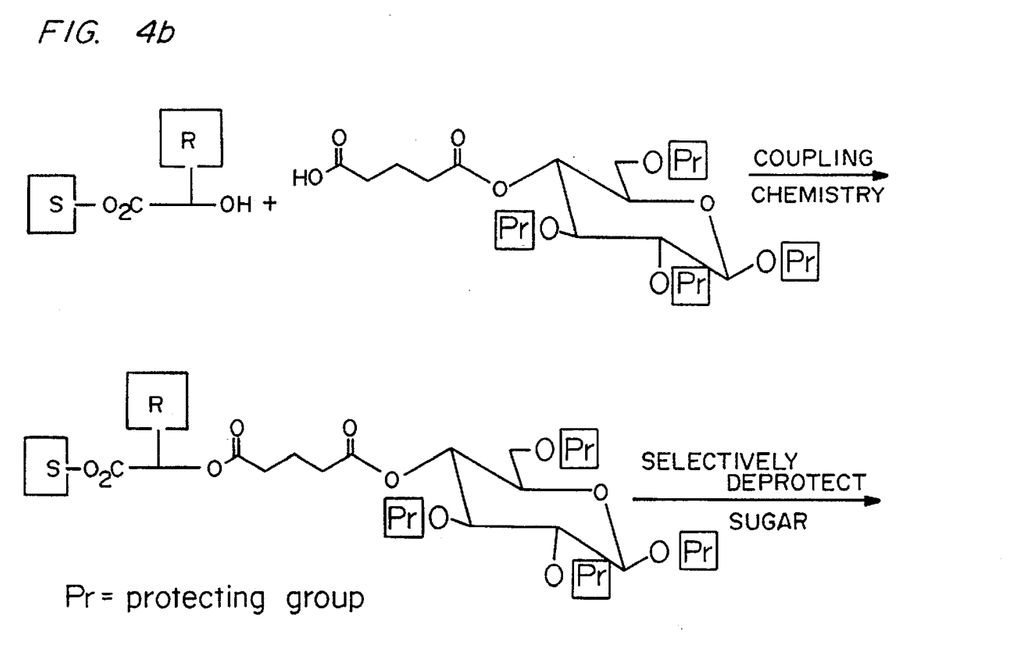

The method of incorporation depends on whether the oligomer is being elongated by reacting the carboxy group or derivative on an oligomer with a hydroxy, thio or amine group on a molecule to be incorporated, or by reacting a hydroxy, thio or amine group on an oligomer with a carboxy group or derivative on a molecule to be incorporated. Both methods of incorporating a nucleotide are illustrated in FIGS. 3a and 3b, from the carboxyl terminal end and the hydroxyl terminal end, respectively. Both methods of incorporating a sugar are illustrated in FIGS. 4a and 4b, from the carboxyl terminal end and the hydroxyl terminal end, respectively.

If an oligomer is being elongated by reacting the carboxy group or derivative on the oligomer with a hydroxy group on a sugar, then one protects all hydroxy or other functional groups that are not involved in the coupling step and could interfere with the coupling step, and reacts the remaining hydroxy group with the carboxylic acid or derivative on the oligomer. If an oligomer is being elongated by reacting a hydroxy, thio or amine group on the oligomer with a carboxy group or derivative on the molecule to be incorporated, then a hydroxy or other functional group on the sugar must be converted to a suitably reactive functionality, such as a carboxylic acid derivative, to effect the coupling, as described above.

A hydroxy, thio or amine group on a sugar can be converted, for example, to a carboxylic acid derivative by reaction with a compound of the formula wherein n is between 0 and 25 and p is 0 or 1 and $R^6$ are the same or different.

The resulting carboxylic acid derivative can then be reacted with a free hydroxy, thio or amine group on the oligomer. After the coupling is complete, a hydroxy or other functional group must be deprotected to react with the next molecule to be incorporated into the oligomer, if desired. Alternatively, one could convert a group on the sugar to an alkyl halide or other group reactive with a terminal group on the oligomer.

5. Incorporation of Peptides.

Figures 5A, 5B:
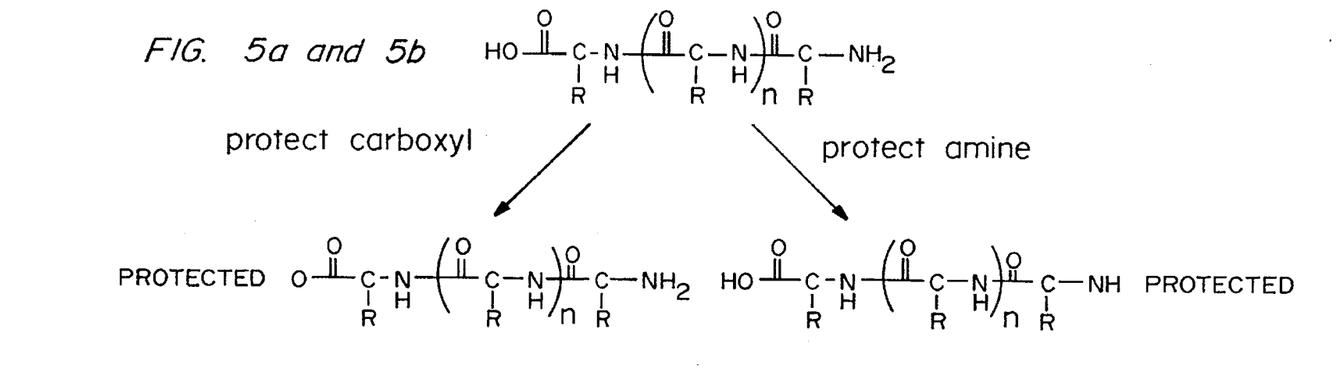
FIGS. 5a and 5b are schematic illustrations of a process for incorporating a peptide into an oligomer, with synthesis from the C-terminal end (FIG. 5a) or the O-terminal end (FIG. 5b).
Figure 5A:
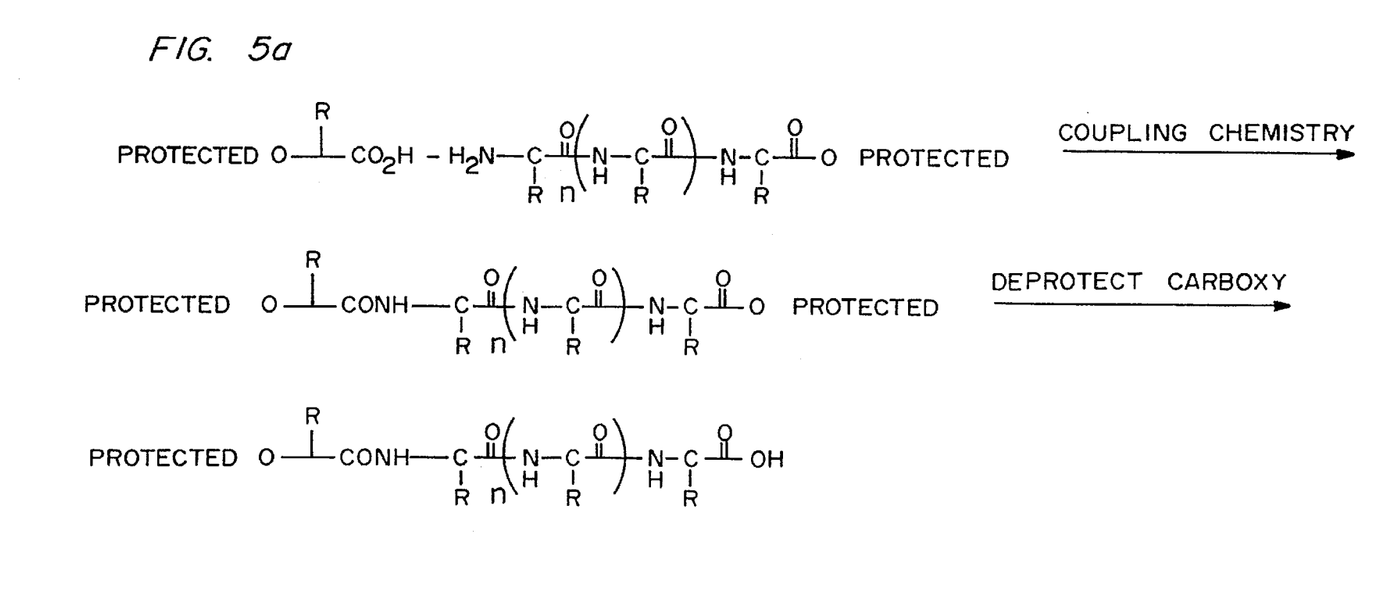
Figure 5B:
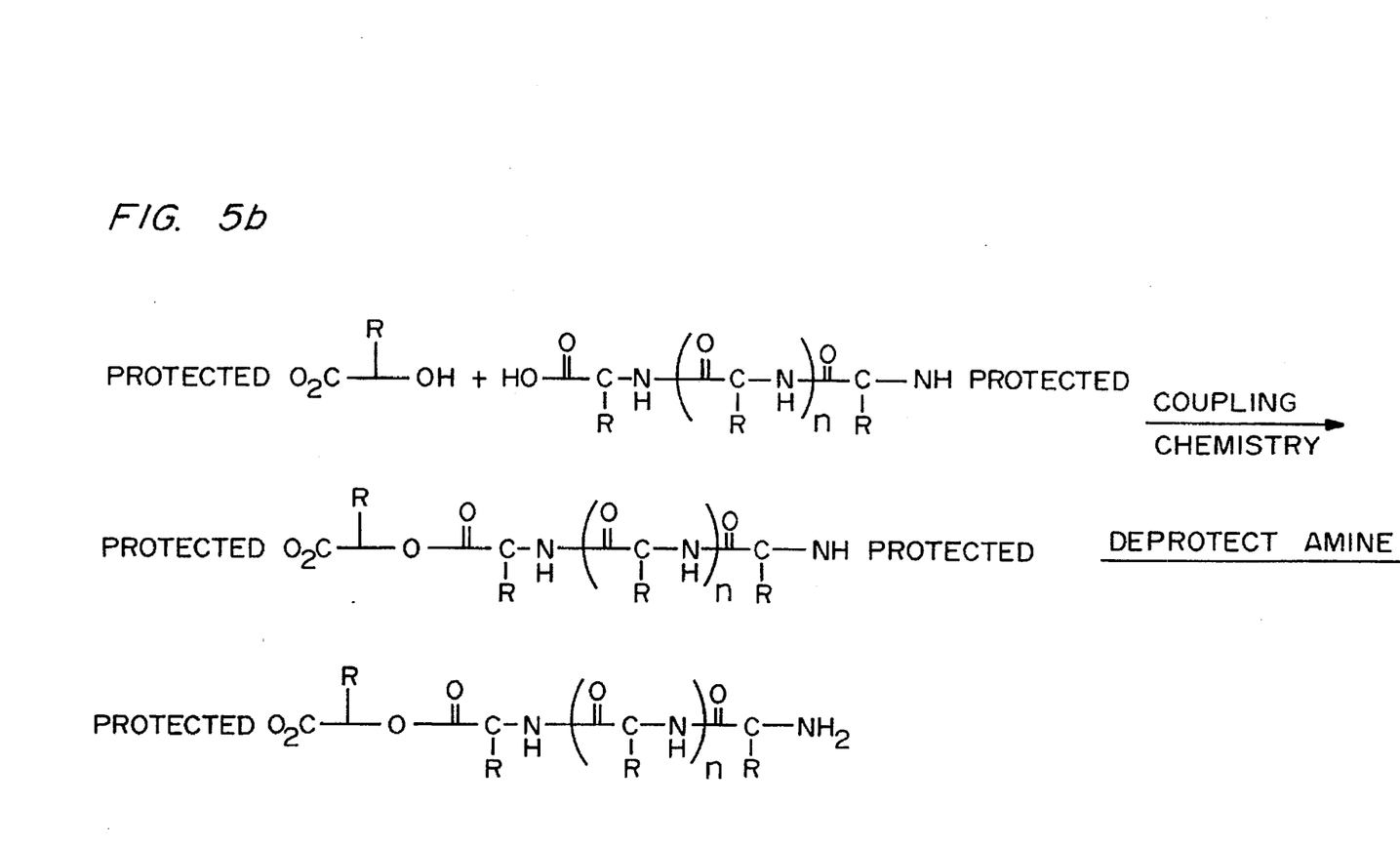

Peptides can be incorporated into an oligomer, whether elongating the oligomer from the C-terminal or O-terminal ends. Both of these methods are illustrated in FIGS. 5a and 5b, respectively. Peptides contain a free carboxylic acid and amine group, and optionally contain other functional groups. Any reactive functional group not involved in the coupling reaction must be protected, as discussed below.

If an oligomer is being elongated from the C-terminal end of the oligomer, the carboxy group on the peptide must be protected, and the amine group on the peptide must be available for reaction. The amide linkage can be formed by dehydrating the amine and carboxy groups, or by other amidation reactions. After the amide linkage is formed, the carboxy group on the peptide is deprotected.

Reaction of carboxyl derivatives with amine functionalities can often be carried out in protic solvents, since the amine is often more nucleophilic than the protic solvent. Suitable solvents can include protic solvents such as water and alcohols such as methanol, ethanol, and propyl alcohol, and aprotic solvents such as dialkyl formamides, such as dimethylformamide, dialkyl sulfoxides, such as dimethylsulfoxide, aromatic solvents such as benzene, toluene, and xylenes, chlorinated solvents such as dichloromethane, chloroform, and trichloroethane, and ethers such as tetrahydrofuran and dibutyl ether. The pH of the reaction can be controlled by adding an aprotic base, such as trialkyl amines or pyridine, or with lithium, sodium or potassium hydroxide.

If an oligomer is being elongated from the O-terminal end of the oligomer, the amine group on the peptide must be protected, and the carboxy group on the peptide must be available for reaction. After the amide linkage is formed, the amine group is deprotected so that it can react with the next molecule to be incorporated into the oligomer.

C. Coupling of a Monomer to a Solid Support.

1. Selection of solid support

The solid support may at any time be either soluble or insoluble in the reaction media. See, for example, Bayer, E., Angew. Chem. Int. Ed. Engl., 30, 113–129 (1991). Useful solid supports must contain a functional group which reacts with carboxy or hydroxy groups, and optionally, thio or amine groups to form a covalent bond. Ideally, these supports are polymeric resins which can be recycled after the oligomer synthesis is complete, and the oligomer is removed from the support. For certain applications, however, if may be desirable to leave the oligomer bound to the solid support. Requirements for the solid-phase support depend primarily upon the direction of elongation and the stability of the oligomer, and to a lesser degree on the side-chain protecting groups. O-terminal and C-terminal attachment to a solid support and elongation are described separately, as shown in FIGS. 2a and 2b.

Examples of useful solid supports include, but are not limited to, 4-(oxymethyl)phenyl acetamidomethyl poly (styrene-co-divinylbenzene); styrene-divinylbenzene copolymer-anchored dimethyl- and diphenyl-chlorosilanes; styrene-divinylbenzene copolymer-anchored trityl chlorides; p-hydroxyphenyl propionic poly(styrene-co-divinylbenzene); 4-(2',4'-dimethoxyphenyl-hydroxymethyl)-phenoxymethylpolystyrene; styrene-divinylbenzene copolymer-anchored o-nitrobenzyl esters; kieselguhrpoly-dimethylacrylamide; nitroveratryloxycarbonyl linked glass (via aminopropyltriethoxysilane), otherwise known as silanized glass-anchored nitroveratryloxycarbonyl); p-hydroxymethyl phenoxymethyl polystyrene; p-methylbenzhydrylamine; PAC™; PAL™; and PEG-PS™ supports. Many other types of resin are either known or can be modified to fit the criteria defined below for elongation.

In both cases described below, the terminus not bound to the solid support is preferably, though not required, to be masked by a protecting group.

2. Attachment to and Cleavage from the solid-phase support.

The method of attachment of the first hydroxy acid to a solid support, via the hydroxyl group, must be compatible with subsequent elongation steps. If the oligomer is to be released from the support, the method of cleavage of the anchoring bond must not harm the oligomer. One method of attachment involves forming a silyl ether between the hydroxy acid and a silyl group on the solid phase support, as described by Danishefsky, S. J., et al., Science, 260, 1307–1309 (1993). After synthesizing the oligomer, this bond is cleaved by either fluoride or mildly acidic conditions that do not damage the oligomer. A second possible method involves attaching the hydroxy group on the first hydroxy acid to form a trityl ether, as described by Chan, T. -H. and Huang, W. -Q., J. Chem. Soc., Chem. Commun., 909–911 (1985); Fyles, T. M. and Leznoff, C. C., Can. J. Chem., 54, 935–942 (1976); and Fyles, T. M., Leznoff, C. C. and Weatherston, J., Can. J. Chem., 55, 4135–4143 (1977). This bond is selectively cleaved by mildly acidic conditions which leave the ester bonds in the oligomer intact.

The following examples represent methods of attaching and cleaving the oligomer from the solid support, as shown in FIGS. 2a and 2b. In most of the methods for attachment, an ester linkage is formed between the carboxy group on the hydroxy acid and a hydroxy group on the solid-phase support. Differences in the resins allow cleavage of the oligomer from the support under a variety of different conditions.

A first method involves hydrolyzing the ester with 10% acetic acid, as described by Rink, H., Tetrahedron Lett., 28, 3787–3790 (1987). In a second method, the ester linkage is hydrolyzed with 50% trifluoroacetic acid (TFA)/ dichloromethane ($CH_2Cl_2$), as described by Mitchell, A. R., et al., J. Org. Chem., 43, 2845–2851 (1978) and Wang, S. -S., J. Am. Chem. Soc., 95, 1328–1333 (1973). In another method, a photosensitive ester linkage is formed between the carboxy group on the hydroxy acid and a hydroxy group on the solid-phase support, and is hydrolyzed by photolysis at 350 nm, as described by Barany, G. and Albericio, F., J. Am. Chem. Soc., 107, 4936–4942 (1985). In still another method, the ester is hydrolyzed with hydrofluoric acid (HF)/Dimethyl sulfide (DMSO), as described by Tam, J. P., et al., J. Am. Chem. Soc., 105, 6442–6455(1983). Another method involves forming an amide linkage between the carboxy group on the hydroxy acid and an amine group on a solid support phase, and hydrolyzing the amide enzymatically, as described by Jones, J. B., Tetrahedron, 42, 3351–3403 (1986) and references cited therein; Whitesides, G. M. and Wong, C. -H., Angew. Chem. Int. Ed., 24, 617–638 (1985). An amide bond is difficult to cleave chemically without damaging the oligomer.

D. Protecting Groups.

The protecting groups Y and Z, and the activating group X, shown in FIGS. 1a and 1b, can be selected from an almost endless list. Specific requirements, reflecting the need for selectivity in deblocking, coupling and possibly side-chain masking, however, mean that selection of X, Y and Z for optimum performance and yield in the oligomer synthesis will be dependent on the groups on the units being incorporated into the oligomer.

1. For hydroxyl groups.

Suitable masking groups (Y) for the hydroxyl group include, but are not limited to, certain ethers, esters and carbonates (Greene, T. W. and Wuts, P. G. M., "Protective groups in organic synthesis," John Wiley, New York, 2nd Ed. (1991)). Examples of these groups, and conditions for their removal, are listed in Table I:

TABLE 1

Protecting Groups for the Hydroxyl Group

| Protecting Group Y | Cleavage Conditions |
| --- | --- |
| 1. 9-Fluorenylmethoxycarbonate (Fmoc) | Triethylamine |
| 2. 3,5-Dimethoxyphenyl-2-propylcarbonate (Ddz) | 1–5% Trifluoroacetic acid |
| 3. Trifluoroacetyl ($CF_3CO_2$) | Aqueous solution pH7 |
| 4. Benzyl ether (BnO) | Hydrogenolysis |
| 5. Triethylsilyl ether ($Et_3SiO$) | Fluoride or Acid |
| 6. Tetrahydropyranyl ether (THP) | Acetic Acid |
| 7. Di(p-methoxyphenyl)phenylmethyl ether (DMTr) | 3% Trichloroacetic acid |
| 8. o-Nitrobenzyl ether ($o$-$NO_2C_6H_4CH_2O$) | Photolysis |

2. For Carboxyl Groups.

Suitable protecting groups (Z) for the carboxyl group include, but are not limited to, the esters listed in Table II, and described in Green and Wuts, Protecting Groups in Organic Synthesis, John Wiley (1991):

TABLE II

Protecting Groups for the Carboxyl Group

| Protecting Group Z | Cleavage Conditions |
| --- | --- |
| 1. 9-Fluorenylmethyl ester (Fm) | Piperidine |
| 2. t-Butyl ester | Trifluoroacetic Acid |
| 3. Benzyl ester | Hydrogenolysis |
| 4. o-Nitrobenzyl ester | Photolysis |
| 5. t-Butyldimethylsilyl ester (TBDMS) | Acetic acid or fluoride |
| 6. Carboxylate anion | None required |
| 7. Nitroveratryl ester (NVOC) | Photolysis |

3. For Side-Chain Functionalities.

As with other solid-phase synthetic methods, functionality in the hydroxy acid monomers (designated $R^1$ and $R^2$ in FIGS. 1a and 1b), or in any other monomer to be incorporated into the oligomer, must not interfere with coupling processes, cause racemization of the hydroxy acid units if chirality is present, and should allow the oligomer to be detached from the solid support if this is desired. Side-chain functionalities such as carboxylic acids, alcohols, and amines may interfere with the oligomer synthesis and these groups must be appropriately protected. The choice of protecting groups which can be used depends on the solid-phase, the direction of synthesis, the coupling procedure, and the timing of deprotection.

As used herein, "side-chain functionality" refers to functional groups, such as hydroxy, thio, amine, keto, carboxy, alkenyl, alkynyl, carbonyl, and phosphorus derivatives such as phosphate, phosphonate and phosphinate in the hydroxy, thio, or amino acid monomer, or in a sugar, peptide, or nucleotide moiety, that is not involved in coupling to form an ester, thioester, or amide bond. Side chain functionality can be present in the oligomer backbone, in the monomer to be incorporated into the oligomer, or in any side chain on the oligomer or monomer.

Examples of suitable protecting groups are well known to those skilled in the art. See, generally, Greene and Wuts, Protecting Groups in Organic Chemistry, John Wiley (1991). The term "protecting group" as used herein refers to a moiety which blocks a functional group from reaction, and which is cleavable when there is no longer a need to protect the functional group.

The options available for protecting functionalities depend on whether deprotection must occur before the oligomer is released from the solid support or after its release from the support. In the latter case, protecting group strategies can be more flexible. Suitable protecting groups for some other side-chain groups are described in "Protective groups in organic synthesis," and listed in Table III.

Examples of protecting groups for thiol groups include, but are not limited to, S-benzyl thioether, S-9-fluorenylmethyl thioether, S-trityl, and S-acetylmercaptoacetyl (SAMA).

Examples of protecting groups for amine groups include, but are not limited to, t-butyloxycarbonyl (Boc), benzyloxycarbonyl (Cbz), o-nitrobenzyloxycarbonyl, and trifluoroacetamide (TFA).

TABLE III

Examples of Protecting Groups for Various Side-Chain Functionalities.

| Side-chain Group | Possible Protecting Groups |
| --- | --- |
| 1. Amino | t-Butyloxycarbonyl (Boc) |
|  | Benzyloxycarbonyl (Cbz) |
|  | o-Nitrobenzyloxycarbonyl |
|  | Trifluoroacetamides (TFA) |
| 2. Thiol | S-9-Fluorenylmethyl thioether |
|  | S-Benzyl thioether |
| 3. Carbonyl | 1,3-Dioxolanes |
| 4. Phenol | Benzyl ether |
| 5. Guanidino | N-nitroamine |
| 6. Imidazole | t-Butyloxycarbonyl (BOC) |
| 7. Phosphinic Acid | Phosphinate methylester |

As discussed above in forming ester linkages, any interfering functional group not involved in the coupling step, or in a side chain, must be protected. Selective protection of hydroxy groups in the presence of thio or amine groups is known to those skilled in the art. Amine groups are typically more reactive than hydroxy or thio groups. For molecules containing amine and hydroxy and/or thio groups, a preferred strategy for selectively protecting the hydroxy or thio groups is to protect the amine group with a labile protecting group, protect the hydroxy or thio group, and subsequently remove the labile amine protecting group. As used herein, the term "labile," refers to an unstable ligand that is susceptible to hydrolytic or enzymatic cleavage in vivo. As used herein, the term "selective deprotection" refers to removing a protecting group from one part of a molecule, while leaving other protecting groups intact. The term "enzymatic deprotection" is defined as use of an enzyme to cleave an ester, thioester or amide linkage. One can enzymatically deprotect esters with esterases and amide linkages with either amidases or proteases. In this manner, a hydroxy or thio group can be protected, and an amine group made available for forming an amide linkage.

Protection of hydroxy groups in sugars and nucleotides is well known, and is described in "Protective Groups in Organic Chemistry", McOmie ed pp. 100–101, 121, 127, 128, and 129 (Plenum Press, London and New York, 1973), hereby incorporated by reference.

Cyclic acetals and ketals are often used to protect 1,2- and 1,3-glycol systems in sugar chemistry. The most commonly used ketal group of this type is the isopropylidene ketal. Cyclic isopropylidene ketals have been used more frequently than any other acetal or ketal groups in the protection of glycol systems, and have been used widely in sugar chemistry. The isopropylidene ketal is labile under comparatively mild conditions of acidic hydrolysis. There are so many examples of the use of the isopropylidene protecting group that it is difficult to select representative examples.

Benzyl and trityl ethers are known to survive the hydrolysis conditions which cleave the isopropylidene ketal. One method for selective protection and deprotection of hydroxy groups in sugars involves protecting vicinal hydroxy groups as an isopropylidene ketal, and protecting the remaining hydroxy groups as benzyl or trityl ethers. Since the cleavage conditions are different, one can selectively deprotect hydroxy groups.

Nucleotides typically have hydroxy groups at the 2', 3' and 5'-positions, and a purine or pyrimidine base at the 1' position. The 2' and 3'-hydroxy groups are secondary hydroxy groups, whereas the 5'-hydroxy is a primary hydroxy group. The selective protection and deprotection of the hydroxyl groups on these moieties has been extensively studied. Protection of the amines on the purine and pyrimidine bases has also been extensively studied.

Although the hydroxy groups at the 2' and 3'-positions of the nucleotide are both secondary hydroxy groups, the purine or pyrimidine base at the 1'-position allows the hydroxy groups at the 2' and 3' positions to be selectively protected and deprotected. For example, one can prepare 2', 5'- and 3', 5'-di-o-trityluridines as synthetic intermediates. Primary hydroxyl groups are more readily tritylated than secondary hydroxyl groups.

An isopropylidene ketal can be formed with the 3' and 5'-hydroxy groups, and the 2'-hydroxy group protected with a less labile protecting group. Subsequent hydrolysis of the isopropylidene ketal affords a protected hydroxy group at the 2'-position, leaving the 3' and 5' hydroxy groups open for incorporation into oligomer. The hydroxy group at the 5'-position can then be protected as a trityl group, leaving the hydroxy group at the 3'-position available for incorporation into the oligomer.

Benzyl ethers can be selectively deprotected by treatment with hydrogen, potentially leaving other protected hydroxy groups protected, and allowing one to incorporate the de-benzylated hydroxy group into the oligomer.

From these intermediates, one can covalently link a hydroxyl group at the 2', 3' or 5'-positions with the oligomer, and subsequently deprotect a hydroxyl group at another position. The free hydroxy group can then be reacted to increase the chain length of the oligomer, if desired.

Using the chemistry as outlined above, the hydroxy groups at the 2', 3' and 5'-positions of a nucleotide, or the different hydroxy groups of sugars or other hydroxy containing molecules, can be selectively protected, leaving one hydroxy group for incorporation into the oligomer.

E. Automation

The methods described herein are readily automated for use with apparatus of the type used for automated peptide synthesis. Representative devices are sold by Applied Biosystems, Inc., Foster City, Calif. and Millipore Corporation, Bedford, Mass.

F. Screening for Biological Activity

The oligomers made using the methods described herein can be screened for biological activity using analyzers such as those used by Oncogene Science, Inc. (Uniondale, New York) or Nova Screen. The oligomers can be tested for activity in in vitro or in vivo assays using methods known to those skilled in the art.

For example, enzyme-linked immunosorbent assays can be used to identify oligomers inhibiting binding of antibody to antigen, radiolabelled-receptor binding assays to identify high affinity oligomer ligands or bacterial growth inhibition assays to identify potent antimicrobial oligomers. Examples of these techniques are described in Houghten, R. A. et al., Biotechniques, Vol. 13, pp. 412–421 (1992), hereby incorporated by reference.

A typical assay requires only one to three mg of compound, an amount which can be readily synthesized using the disclosed methods.

Modifications and variations of the present invention will be obvious to those skilled in the art from the foregoing detailed description. Such modifications and variations are intended to come within the scope of the appended claims.

We claim:

1. A method for preparing oligomers of hydroxy acids comprising the steps of a) selecting a first hydroxy acid monomer, b) linking the first hydroxy acid monomer to a solid support via either the terminal carboxy group on the first monomer or the terminal hydroxy group on the first monomer, c) selecting a second hydroxy acid monomer, d) protecting the terminal group on the second hydroxy acid monomer opposite to the terminal group linked to the solid support in step b, e) linking the first monomer and the second monomer through the unprotected terminal groups to form an oligomer bound to a solid support, f) deprotecting the protected terminal group of the second monomer, g) selecting additional hydroxy acid monomers, h) protecting either the terminal carboxy group or the terminal hydroxy group on the additional monomers as necessary to link the additional monomers to the deprotected terminal group, and i) linking the additional monomers to the oligomer, wherein the method further comprises covalently incorporating in place of at least one of the additional hydroxy acid monomers a molecule selected from the group consisting of nucleotides, sugars, thio acids, lipids, steroids, and inorganic molecules, and oligomers thereof, wherein the molecule comprises at least one functional group capable of reacting with at least one terminal group on at least one of the hydroxy acid monomers, thereby to permit the molecule to be covalently incorporated into the oligomer.

2. The method of claim 1 further comprising protecting the functional side groups on the monomers prior to preparing the oligomer, and deprotecting the protected side groups after preparing the oligomer.

3. The method of claim 1 further comprising cleaving the first monomer from the solid support.

4. The method of claim 2 wherein the protecting group is deprotected chemically.

5. The method of claim 2 wherein the protecting group is deprotected enzymatically.

6. The method of claim 1 further comprising activating the terminal carboxylic group prior to reaction with the terminal hydroxyl group.

7. The method of claim 1 wherein the process is automated.

8. A method for preparing oligomers of hydroxy acids comprising the steps of a) selecting a first hydroxy acid monomer, b) linking the first hydroxy acid monomer to a solid support via either the terminal carboxy group on the first monomer or the terminal hydroxy group on the first monomer, c) selecting a second hydroxy acid monomer, d) protecting the terminal group on the second hydroxy acid monomer opposite to the terminal group linked to the solid support in step b, e) linking the first monomer and the second monomer through the unprotected terminal groups to form an oligomer bound to a solid support, f) deprotecting the protected terminal group of the second monomer, g) selecting additional hydroxy acid monomers, h) protecting either the terminal carboxy group or the terminal hydroxy group on the additional monomers as necessary to link the additional monomers to the deprotected terminal group, and i) linking the additional monomers to the oligomer, wherein the method further comprises incorporating a sugar in place of at least one of the additional hydroxy acid monomers by the steps of i) selecting a sugar to be incorporated into the oligomer;

ii) selectively protecting all but one of the reactive hydroxy groups on the sugar;

iii) reacting the unprotected reactive hydroxy group to form a carboxyl derivative; and iv) reacting the carboxyl derivative with an unprotected —OH group on the oligomer.

9. The method of claim 1 wherein the molecule is a nucleotide or oligomer of nucleotides.

10. The method of claim 1 further comprising incorporating an amino acid or oligomer thereof into the oligomer in place of at least one hydroxy acid monomer.

11. A method for preparing oligomers of hydroxy acids comprising the steps of a) selecting a first hydroxy acid monomer, b) linking the first hydroxy acid monomer to a solid support via either the terminal carboxy group on the first monomer or the terminal hydroxy group on the first monomer, c) selecting a second hydroxy acid monomer, d) protecting the terminal group on the second hydroxy acid monomer opposite to the terminal group linked to the solid support in step b, e) linking the first monomer and the second monomer through the unprotected terminal groups to form an oligomer bound to a solid support, f) deprotecting the protected terminal group of the second monomer, g) selecting additional hydroxy acid monomers, h) protecting either the terminal carboxy group or the terminal hydroxy group on the additional monomers as necessary to link the additional monomers to the deprotected terminal group, and i) linking the additional monomers to the oligomer, wherein the method further comprises incorporating a plurality of amino acids into the oligomer in place of at least one of the additional hydroxy acid monomers.

12. The method of claim 11 wherein at least one of the amino acids incorporated is an amino acid oligomer.

13. A method for preparing oligomers of hydroxy acids comprising the steps of a) selecting a first hydroxy acid monomer, wherein the hydroxy acid monomer selected from the group consisting of 3-, 4- and 5- hydroxy acid monomers, b) linking the first hydroxy acid monomer to a solid support via either the terminal carboxy group on the first monomer or the terminal hydroxy group on the first monomer, c) selecting a second hydroxy acid monomer, d) protecting the terminal group on the second hydroxy acid monomer opposite to the terminal group linked to the solid support in step b, e) linking the first monomer and the second monomer through the unprotected terminal groups to form an oligomer bound to a solid support, f) deprotecting the protected terminal group of the second monomer, g) selecting additional hydroxy acid monomers, h) protecting either the terminal carboxy group or the terminal hydroxy group on the additional monomers as necessary to link the additional monomers to the deprotected terminal group, and i) linking the additional monomers to the oligomer, wherein the method further comprises incorporating an amino acid or oligomer thereof into the oligomer in place of at least one of the additional hydroxy acid monomers.

14. The method of claim 12 wherein the amino acid oligomer is a peptide.

15. The method of claim 13 wherein the amino acid oligomer is a peptide.

16. The method of claim 1 further comprising preparing a plurality of different hydroxy oligomers each comprising a different molecule incorporated therein, and screening the oligomers for biological activity.

17. The method of claim 11 further comprising preparing a plurality of different hydroxy acid oligomers each comprising a different amino acid or oligomer thereof incorporated in the hydroxy acid oligomer, and screening the oligomers for biological activity.

18. The method of claim 1 wherein the terminal carboxy group on the first monomer or the terminal hydroxy group on the first monomer is linked to the solid support via a protecting group.

19. The method of claim 1 wherein the molecule comprises at least one functional group selected from the group consisting of hydroxy, carboxy, thio and amine.

20. The method of claim 19 wherein the molecule comprises first and second functional groups and at least one of the functional groups is protected prior to incorporation.

* * * * *